United States Patent
Yagitani et al.

(10) Patent No.: US 8,729,909 B2
(45) Date of Patent: May 20, 2014

(54) RADIO WAVE INTENSITY MEASURING DEVICE AND RADIO WAVE MEASURING SYSTEM

(75) Inventors: Satoshi Yagitani, Kanazawa (JP); Takao Shimizu, Kanazawa (JP); Yusuke Yamanaka, Kanazawa (JP)

(73) Assignee: Kanazawa University, Ishikawa (JP)

( * ) Notice: Subject to any disclaimer, the term of this patent is extended or adjusted under 35 U.S.C. 154(b) by 313 days.

(21) Appl. No.: 13/056,391

(22) PCT Filed: Jul. 22, 2009

(86) PCT No.: PCT/JP2009/003429
§ 371 (c)(1),
(2), (4) Date: Jan. 28, 2011

(87) PCT Pub. No.: WO2010/013408
PCT Pub. Date: Feb. 4, 2010

(65) Prior Publication Data
US 2011/0128016 A1    Jun. 2, 2011

(30) Foreign Application Priority Data
Jul. 28, 2008    (JP) ................................ 2008-193845

(51) Int. Cl.
| | | |
|---|---|---|
| H04J 3/00 | (2006.01) | |
| H04B 17/00 | (2006.01) | |
| G01R 29/08 | (2006.01) | |
| H03H 7/07 | (2006.01) | |
| G01N 22/00 | (2006.01) | |
| G01N 22/04 | (2006.01) | |
| G01R 1/067 | (2006.01) | |

(52) U.S. Cl.
CPC ............. G01R 29/0878 (2013.01); H03H 7/07 (2013.01); G01N 22/00 (2013.01); G01N 22/04 (2013.01); G01R 1/06772 (2013.01)
USPC .......................... 324/633; 370/280; 455/226.1

(58) Field of Classification Search
CPC ..... G01R 29/0878; H03H 7/07; G01N 22/00; G01N 22/04
USPC ............. 324/633, 631, 133, 76.12–76.14, 84; 370/280; 455/226.1; 342/20; 333/170; 340/447, 539.21; 702/66
See application file for complete search history.

(56) References Cited

U.S. PATENT DOCUMENTS 6,867,665 B2 *    3/2005    Manku et al. ................. 333/171

FOREIGN PATENT DOCUMENTS

| JP | 2003-23288 | 1/2003 |
| JP | 2003-66079 | 3/2003 |

(Continued)

OTHER PUBLICATIONS

Motojima et al., Visualization Device for Radio Wave, May 17, 2007, (see attached English translation).*

(Continued)

*Primary Examiner* — Melissa Koval
*Assistant Examiner* — Farhana Hoque
(74) *Attorney, Agent, or Firm* — Wenderoth, Lind & Ponack, L.L.P.

(57) ABSTRACT

A radio wave intensity measuring device includes a radio wave absorber (100) configured to include a plane having a plurality of cells (CL11, CL12, . . . ) and to absorb a radio wave entering the plane, and a measurer (200) configured to measure radio wave intensities in a plurality of cells.

6 Claims, 15 Drawing Sheets

(56) References Cited

FOREIGN PATENT DOCUMENTS

| | | | |
|---|---|---|---|
| JP | 2007121238 | * | 10/2005 |
| JP | 2006-234582 | | 9/2006 |
| JP | 2006-337281 | | 12/2006 |
| JP | 2007-121238 | | 5/2007 |
| JP | 2007121238 | * | 5/2007 |

OTHER PUBLICATIONS

International Search Report issued Oct. 20, 2009 in International (PCT) Application No. PCT/JP2009/003429.

Full machine translation for Japanese Patent Application Publication No. 2007-121238, published May 17, 2007.
Full machine translation for Japanese Patent Application Publication No. 2003-23288, published Jan. 24, 2003.
Full machine translation for Japanese Patent Application Publication No. 2006-337281, published Dec. 14, 2006.
Full machine translation for Japanese Patent Application Publication No. 2006-234582, published Sep. 7, 2006.
Full machine translation for Japanese Patent Application Publication No. 2003-66079, published Mar. 5, 2003.

* cited by examiner

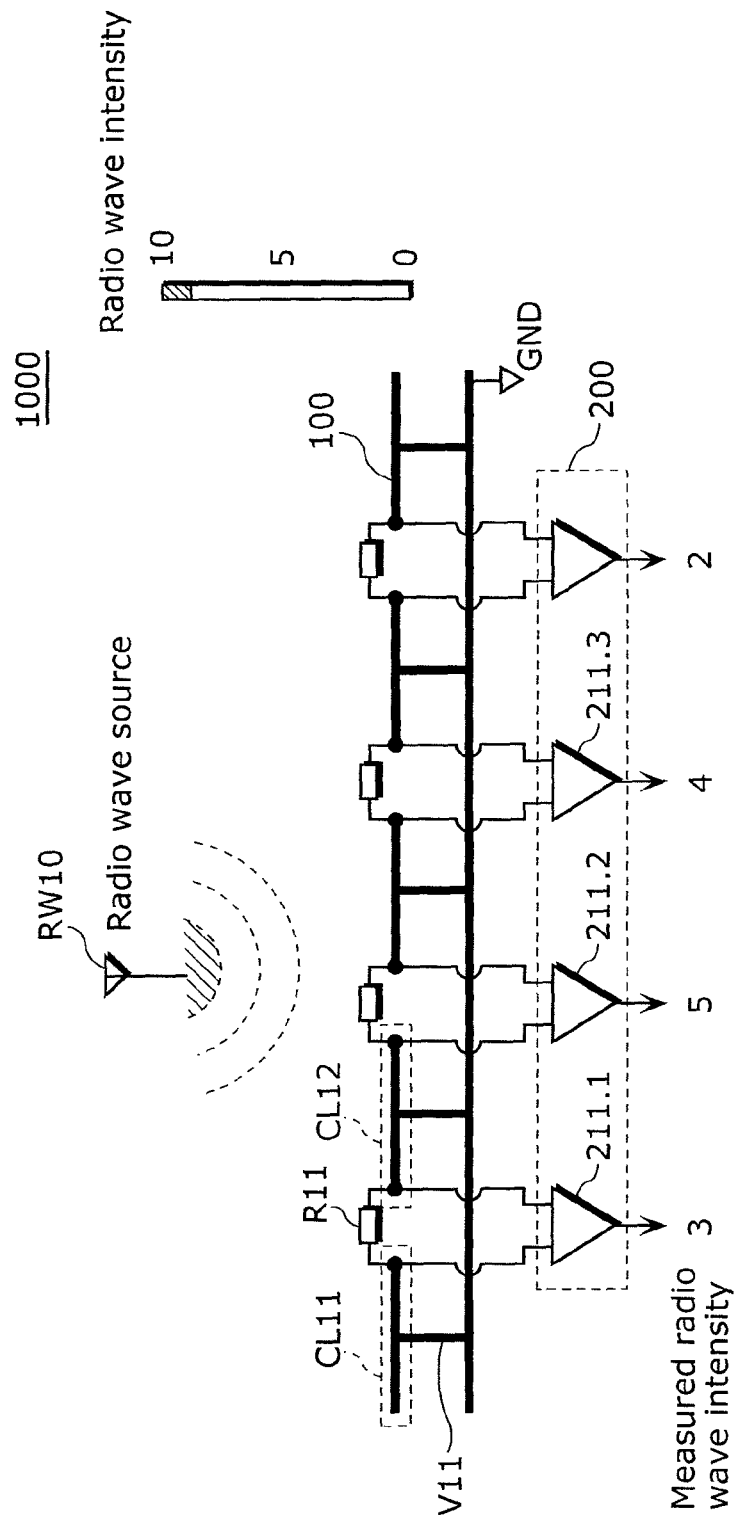

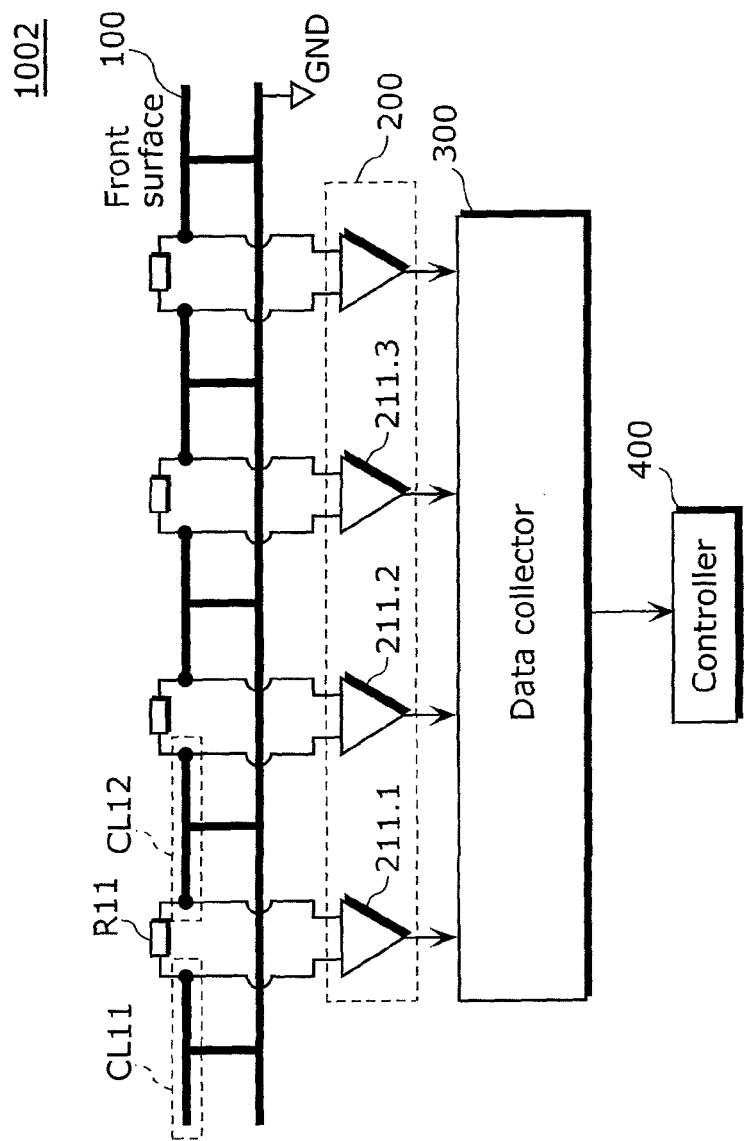

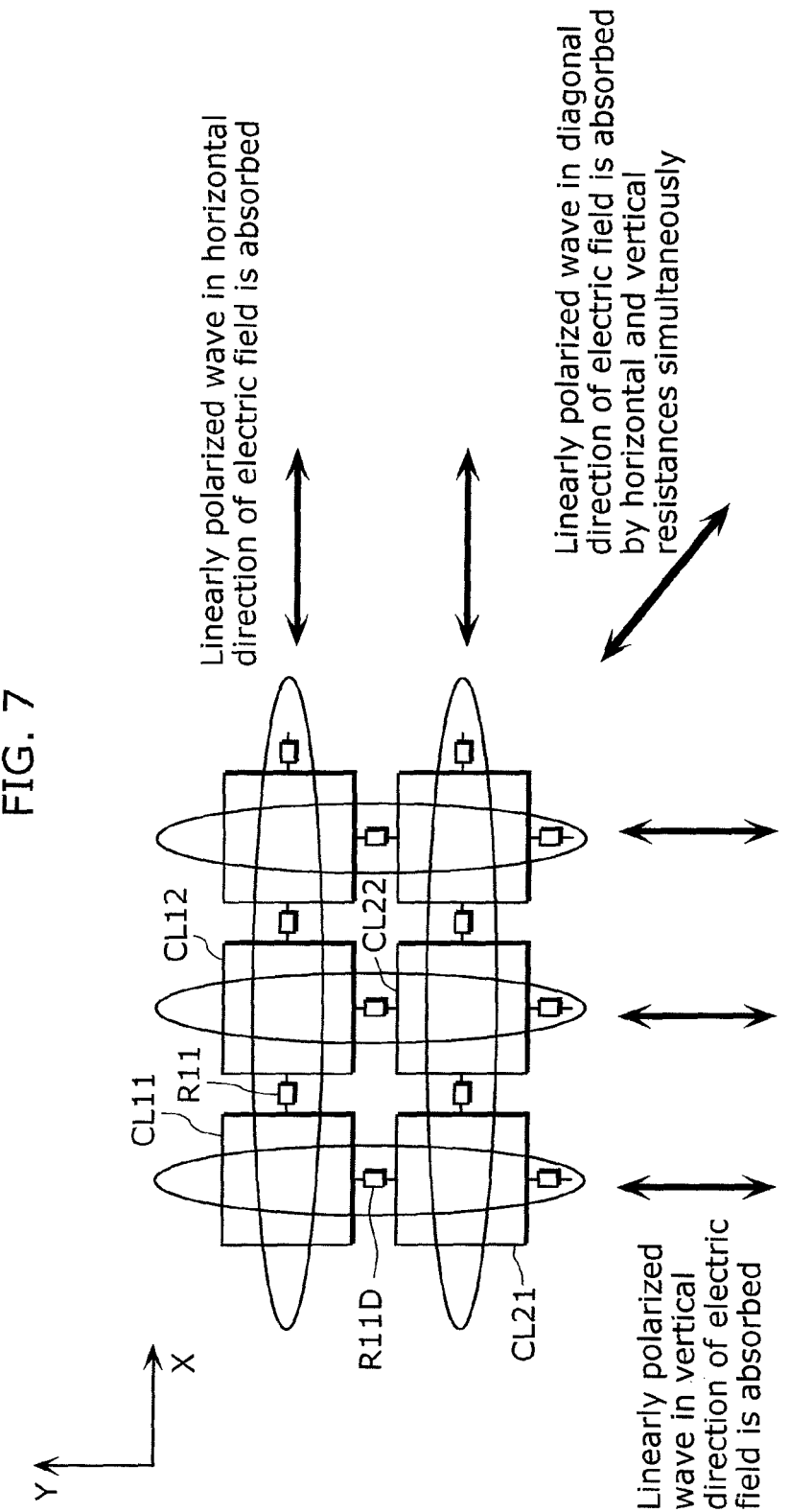

Equivalent circuit

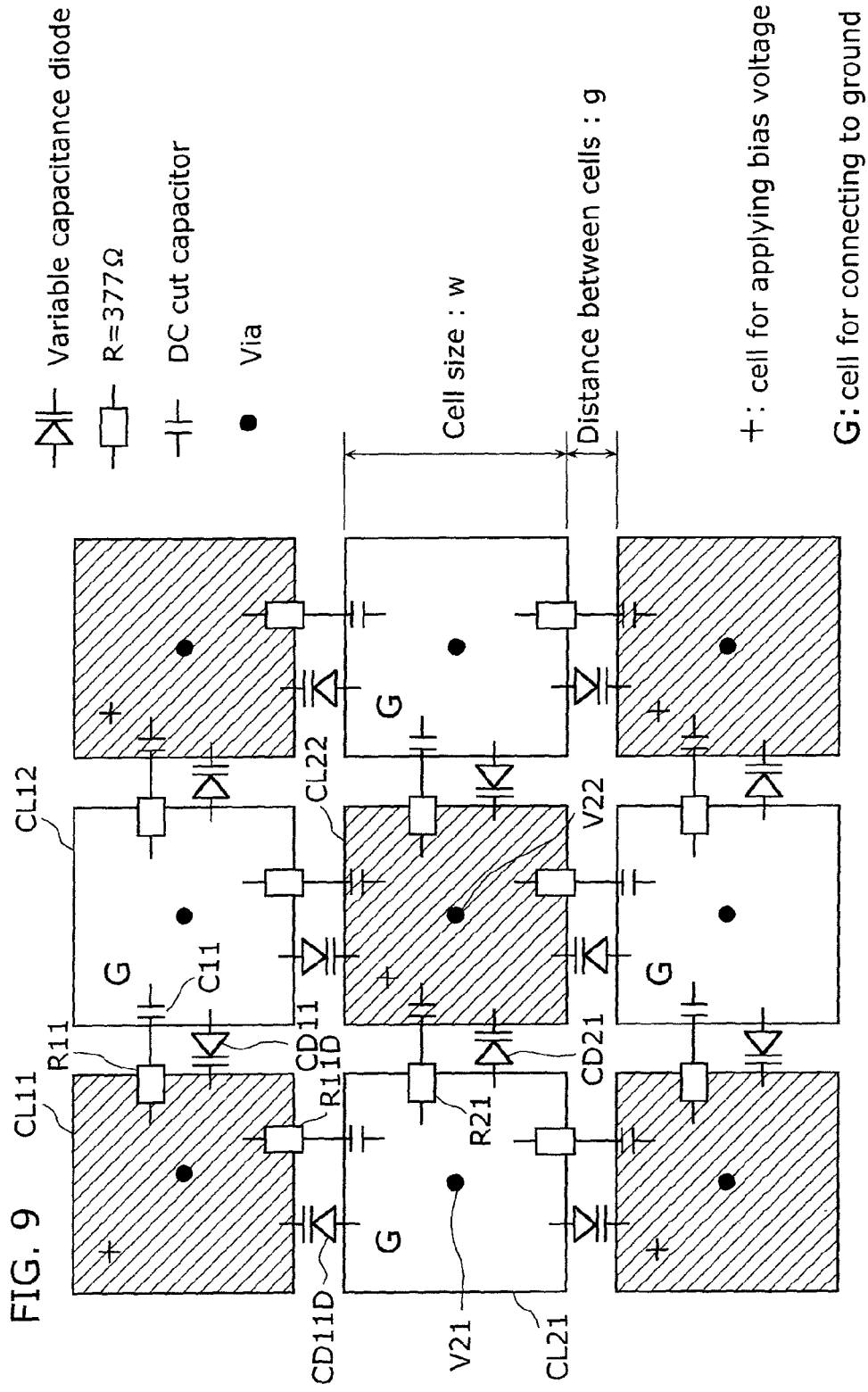

FIG. 14

RADIO WAVE INTENSITY MEASURING DEVICE AND RADIO WAVE MEASURING SYSTEM

TECHNICAL FIELD

The present invention relates to a measuring device for measuring radio wave intensity and a radio wave intensity measuring system.

BACKGROUND ART

In order to identify the portions of various electronic devices, from which a radio wave (electromagnetic wave) noise is actually radiated, it is important to recognize the spatial distribution of the radio wave noise around the device. Also, when the directivity of an antenna built into a communication device is evaluated, the spatial distribution of radiated radio wave intensity needs to be measured. PTL 1 discloses a technology (hereinafter referred to as a conventional technology A), in which the spatial distribution of radio wave intensity is measured by sequentially shifting an electromagnetic field probe through a plurality of measurement points.

CITATION LIST

Patent Literature

Japanese Unexamined Patent Application Publication No. 2003-66079

SUMMARY OF INVENTION

Technical Problem

However, in order to measure the radio wave intensities in a plurality of measurement sections (the measurement points) with the conventional technology A, the electromagnetic field probe needs to be sequentially shifted through the plurality of measurement sections. Accordingly, it is difficult to measure the radio wave intensities in a plurality of measurement sections in a short period of time with the conventional technology A.

The present invention is provided to solve the above-mentioned problem, and it is an object of the invention to provide a radio wave intensity measuring device and a radio wave intensity measuring system capable of measuring the radio wave intensities in a plurality of measurement sections in a short period of time.

Solution to Problem

In order to solve the above-described problem, according to an aspect of the present invention, a radio wave intensity measuring device for measuring a radio wave intensity includes a radio wave absorber that has a plane with a plurality of measurement sections, and is configured to absorb the radio wave incident on the plane; and a measurer configured to measure radio wave intensities in the plurality of measurement sections.

Preferably, a measuring member is disposed in a neighborhood of each of the measurement sections, and the measurer is configured to measure the radio wave intensities in the respective measurement sections by using the measuring member disposed in the neighborhood of each of the measurement sections.

Preferably, the plurality of measuring members are disposed in a matrix form, and the radio wave intensity measuring device further includes a polarization direction identifying unit configured to identify a polarization direction of radio wave based on an intensity of the radio wave measured by the measurer which uses partial measuring members aligned in a row direction out of the plurality of measuring members, and an intensity of the radio wave measured by the measurer which uses partial measuring members aligned in a column direction out of the plurality of measuring members.

Preferably, the wave absorber includes a plurality of resonant circuits that absorb radio wave at a maximum level when a resonance occurs, and further includes a resonance frequency changer that changes a resonance frequency of each of the resonant circuits.

Preferably, the measurer includes a plurality of measuring circuits that measure respective radio wave intensities in the plurality of measurement sections almost simultaneously.

Preferably, the radio wave intensity measuring device further includes a data collector configured to scan and collect a plurality of radio wave intensities measured by the respective measuring circuits.

The radio wave intensity measuring system according to another aspect of the present invention includes the radio wave intensity measuring device and a display device. The radio wave intensity measuring device further includes a transmitter configured to transmit the plurality of radio wave intensities collected by the data collector to the display device; the display device includes an image generator configured to generate a radio wave intensity distribution image which is an image visualized by associating the plurality of radio wave intensities with respective locations of the measurement sections based on the plurality of radio wave intensities received from the transmitter, and a displayer configured to display the radio wave intensity distribution image generated by the image generator.

Preferably, the plurality of measuring circuits measure respective radio wave intensities in the plurality of measurement sections for every predetermined time period, the image generator is configured to generate the radio wave intensity distribution image based on the plurality of radio wave intensities measured by the respective plurality of measuring circuits for every predetermined time period, and the displayer is configured to display the radio wave intensity distribution image generated by the image generator for every predetermined time period, while updating the radio wave intensity distribution image.

Advantageous Effects of Invention

The radio wave intensity measuring device according to the present invention measures radio wave intensities in a plurality of measurement sections of the plane belonging to a wave absorber. Therefore, the radio wave intensities in a plurality of measurement sections can be measured in a short period of time.

The radio wave intensity measuring system according to the present invention includes a radio wave intensity measuring device that measures the radio wave intensities in a plurality of measurement sections of the plane belonging to the radio wave absorber. Therefore, the radio wave intensities in a plurality of measurement sections can be measured in a short period of time.

BRIEF DESCRIPTION OF DRAWINGS

FIG. 5 is a diagram showing the configuration of a radio wave intensity measuring device in Embodiment 1.

FIG. 6 is a block diagram showing the configuration of a radio wave intensity measuring device in Embodiment 2.

FIG. 7 is a diagram for illustrating absorption of the electric field of radio wave incident on the front surface of the radio wave absorber.

FIG. 9 is a diagram showing in detail the configuration of the radio wave absorber.

FIG. 14 is a block diagram showing the configuration of a radio wave intensity measuring system in Embodiment 5.

DESCRIPTION OF EMBODIMENTS

In the following, the embodiments of the present invention are described with reference to the drawings. In the following description, the same reference symbols are assigned to the same components. The names and functions of those components are also the same. Accordingly, detailed description related to such components is not repeated.

Embodiment 1

Figure 1:
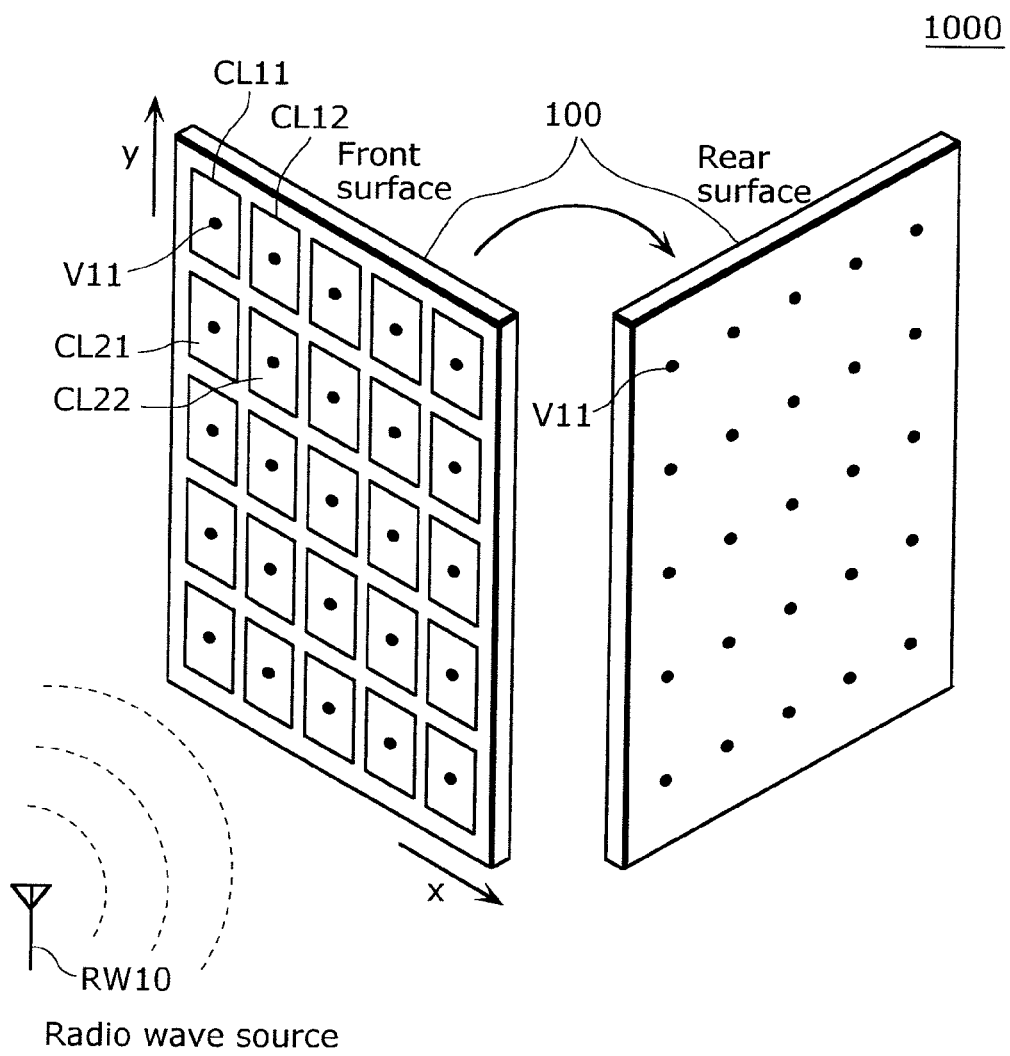
FIG. 1 is a diagram showing the appearance of a radio wave absorber which is a part of a radio wave intensity measuring device in Embodiment 1.

FIG. 1 is a diagram showing the appearance of a radio wave absorber 100 which is a part of a radio wave intensity measuring device 1000 in Embodiment 1. The radio wave intensity measuring device 1000 is a device for measuring radio wave intensity.

As shown in FIG. 1, the radio wave intensity measuring device 1000 is provided with the radio wave absorber 100. The shape of the radio wave absorber 100 is sheet-like (thin plate-like). The front surface of the radio wave absorber 100 absorbs the radio wave emitted from a radio wave source RW10. The radio wave absorber 100 is a dielectric substrate (printed circuit board). The radio wave absorber 100 is not limited to the dielectric substrate, and may be other type of substrate. The radio wave absorber 100 is supposed to have a size which can be easily carried by a measuring operator.

On the front surface of the radio wave absorber 100, a plurality of cells (cell CL11, CL12, . . . , CL21, CL22, . . . ) are disposed in a matrix form. Hereinafter, each cell disposed on the front surface of the radio wave absorber 100 is denoted by cell CL. Thus, each of cell CL11, CL12, . . . , CL21, CL22 is also denoted by cell CL. Each of a plurality of cells CL is a rectangular electrode formed with a copper plate. The shape of the cell CL is not limited to a rectangle, and may be other shape such as a triangle or a hexagon.

The respective plurality of cells CL on the front surface of the radio wave absorber 100 are disposed in a matrix form with an interval sufficiently shorter than the wavelength of the radio wave emitted from the radio wave source RW10. In addition, vertical, and horizontal lengths (sizes) of each of the plurality of cells CL disposed on the front surface of the radio wave absorber 100 are supposed to be sufficiently shorter than the wavelength of the radio wave emitted from the radio wave source RW10.

The frequency of the radio wave emitted from the radio wave source RW10 is supposed to be between 800 MHz and 2.4 GHz as an example. Note that the wavelength of the radio wave with a frequency of 800 MHz is 37.5 cm. The wavelength of the radio wave with a frequency of 2.4 GHz is 12.5 cm. In this case, for example, the interval between the cell CL11 and the cell CL12 is 1 millimeter as an example. For example, vertical and horizontal lengths of the cell CL11 is 20 millimeters as an example. Hereinafter, radio wave incident on the front surface of the radio wave absorber 100 is referred to as a front surface incident radio wave.

The rear surface of the radio wave absorber 100 is covered with a copper plate serving as the ground. The rear surface of the radio wave absorber 100 is not limited to the copper plate, and may be other metal plate. Hereinafter, the rear surface of the radio wave absorber 100 is referred to as a ground surface. Each surface of a plurality of cells CL disposed on the front surface of the radio wave absorber 100 is electrically connected to the ground surface with a short pin (hereinafter referred to as a via). For example, the surface of the cell CL11 is electrically connected to the ground surface with a via V11.

Although the details are described later, a plurality of measuring circuits for measuring the intensity of the radio wave emitted to the front surface of the radio wave absorber 100 are disposed on the rear surface of the radio wave absorber 100.

Figure 2:
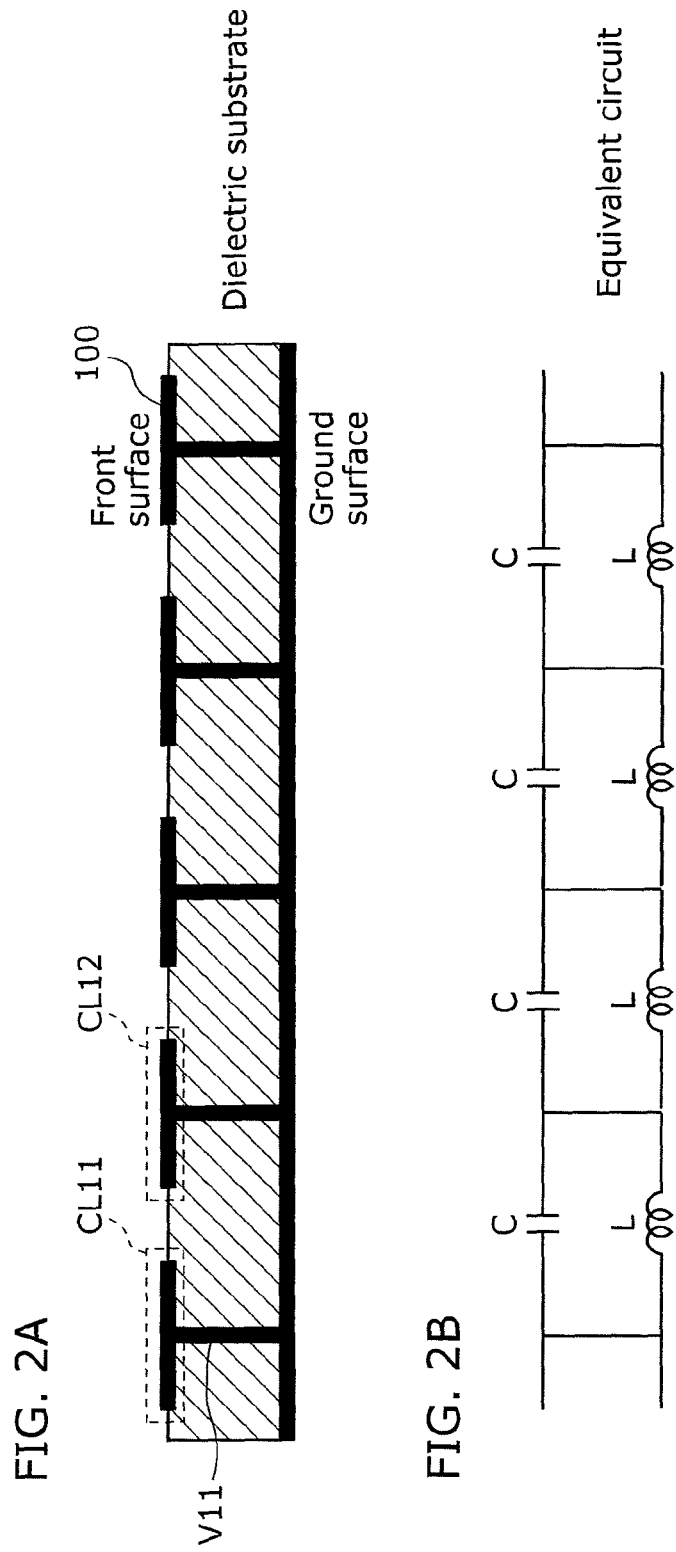
FIG. 2A is a diagram for illustrating a cross-section of the radio wave absorber.
FIG. 2B is a diagram for illustrating a cross-section of the radio wave absorber.

FIGS. 2A and 2B are the diagrams for illustrating a cross-section of the radio wave absorber 100. FIG. 2A is a cross-sectional view of the radio wave absorber 100. Although the later-described resistances are each disposed between each pair of adjacent cells CL on the front surface of the radio wave absorber 100, the resistances are not shown for the simplicity of the illustration.

By using the configuration of the cross-sectional view of the radio wave absorber 100 as shown in FIG. 2A, the radio wave absorber 100 equivalently serves as an LC parallel circuit for the front surface incident radio wave as shown in FIG. 2B. That is to say, the radio wave absorber 100 serves as a sheet having an impedance of an LC parallel circuit for the front surface incident radio wave. That is to say, the radio wave absorber 100 has a characteristic of changing the reflection phase of an incident radio wave depending on its frequency, or blocking propagation of the surface wave with a specific frequency band (band gap).

Figure 3:
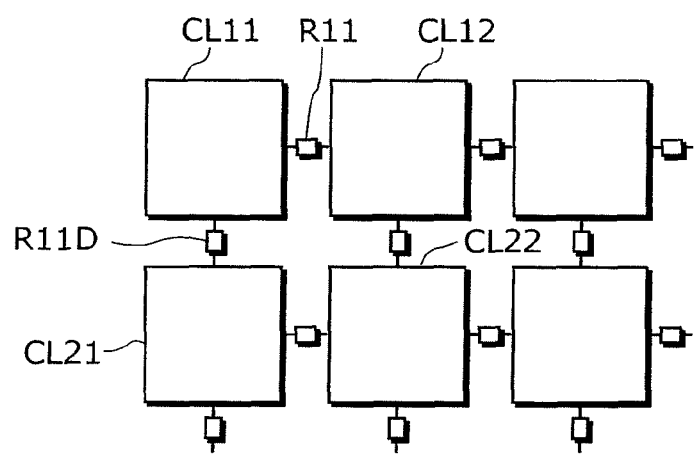
FIG. 3 is a diagram showing in detail a part of a plurality of cells disposed on the front surface of the radio wave absorber.

FIG. 3 is a diagram showing in detail a part of a plurality of cells CL disposed on the front surface of the radio wave absorber 100. As shown in FIG. 3, the plurality of cells CL disposed on the front surface of the radio wave absorber 100 are electrically connected to each other by resistances. For example, the cell CL11 is electrically connected to the cell CL12 via a resistance R11. In addition, the cell CL11 is electrically connected to a cell CL21 via a resistance R11D.

That is to say, one or more resistances are disposed in the neighborhood of each of the plurality of cells CL. As shown in FIG. 3, a plurality of resistances are disposed on the radio wave absorber 100. The plurality of resistances on the radio wave absorber 100 are disposed in a matrix form.

The resistance that connects between each pair of adjacent cells CL disposed on the front surface of the radio wave absorber 100 consumes the electric power (energy) of the radio wave absorbed by the cells CL that are connected to the resistance. The value of the resistance that connects between each pair of adjacent cells CL is 377 ohms as an example.

Figure 4A:
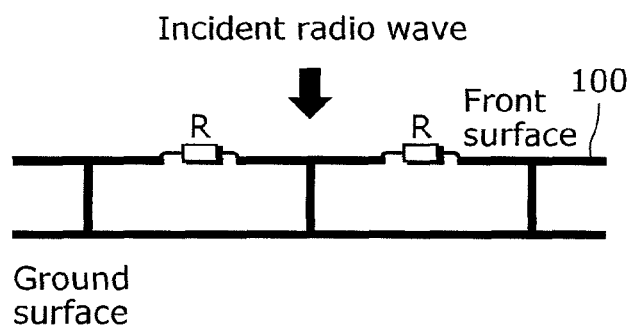
FIG. 4A is a diagram for illustrating a cross-section of the radio wave absorber.
Figure 4B:
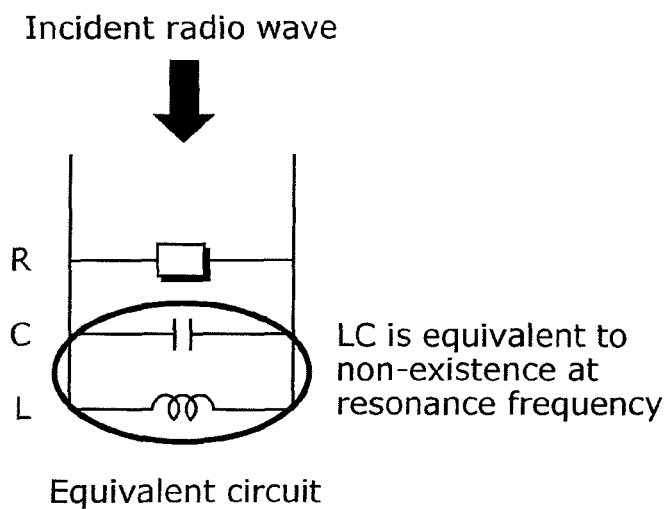
FIG. 4B is a diagram for illustrating a cross-section of the radio wave absorber.

FIGS. 4A and 4B are diagrams for illustrating a cross-section of the radio wave absorber 100. FIG. 4A is a cross-sectional view of the radio wave absorber 100.

By using the configuration of the cross-sectional view of the radio wave absorber 100 as shown in FIG. 4A, the radio wave absorber 100 serves as a circuit, in which a resistance and an LC parallel circuit are connected in parallel, for the front surface incident radio wave as shown in FIG. 4B. The resistance is equivalent to a sheet resistance matched to the wave impedance of free space.

When radio wave having the same frequency as the resonance frequency of the LC parallel circuit enters the front surface of the radio wave absorber 100, the impedance of the LC parallel circuit becomes infinite. In this case, the LC parallel circuit is equivalent to non-existence, and only the sheet resistance is matched with the incident radio wave and absorbs it. The radio wave absorber 100 operates on the same principle as so-called $\lambda/4$ type wave absorber (the thickness of $\frac{1}{4}$ of the wavelength is required), but, by using the structure shown in FIG. 4A, and the equivalent circuit shown in FIG. 4B, the radio wave absorber 100 can be made extremely thinner than the wavelength of the incident radio wave.

FIG. 5 is a diagram showing the configuration of the radio wave intensity measuring device 1000 in Embodiment 1.

As shown in FIG. 5, the radio wave intensity measuring device 1000 further includes a measurer 200. The measurer 200 measures a plurality of radio wave intensities. The measurer 200 includes a plurality of measuring circuits (measuring circuits 211.1, 211.2, 211.3, . . . ). Hereinafter, each of the measuring circuits 211.1, 211.2, 211.3 is also denoted by a measuring circuit 211. That is to say, each measuring circuit included in the measurer 200 is also denoted by a measuring circuit 211.

As shown in FIG. 5, each measuring circuit 211 is electrically connected to both ends of each resistance connected to each of the plurality of cells CL disposed on the front surface of the radio wave absorber 100. For example, the measuring circuit 211.1 is electrically connected to both ends of the resistance R11 which connects between the cell CL11 and the cell CL12. Each measuring circuit 211 measures the electric power consumed by the corresponding resistance.

As described above, the resistance that connects between each pair of adjacent cells CL disposed on the front surface of the radio wave absorber 100 consumes the electric power (energy) of the radio wave absorbed by the cells CL. Accordingly, measuring the electric power consumed by the corresponding resistance using the measuring circuit 211 allows the amount of radio wave absorbed by the corresponding cells CL to be measured. That is to say, the intensity of the radio wave entering the cells CL corresponding to the resistance can be measured by each measuring circuit 211.

In other word, each cell CL disposed on the front surface of the radio wave absorber 100 is a measurement section for measuring the radio wave intensity. The resistance that connects between each pair of adjacent cells CL is a measuring member used to measure the radio wave intensity. The measurement member used to measure the radio wave intensity is not limited to a resistance, and may be other device which has characteristics similar to a resistance.

The measuring circuit 211 is electrically connected to both ends of each resistance connected to each of a plurality of cells CL (cell CL11, CL12, . . . , CL21, CL22, . . . ) disposed in a matrix form on the front surface of the radio wave absorber 100. Accordingly, two-dimensional distribution of the intensity of the front surface incident radio wave can be measured by collecting the radio wave intensities measured by the a respective plurality of measuring circuits 211 included in the measurer 200.

Also, by collecting the radio wave intensities measured by the respective plurality of measuring circuits 211 included in the measurer 200, the spatial distribution of the electric power of the radio wave (i.e., radio wave intensity) that enters the front surface of the radio wave absorber 100 and absorbed by it can be measured without spending time and effort on shifting a sensor such as an electromagnetic field probe in a conventional manner. By repeating the above-mentioned collection of the radio wave intensity, temporal variation in the spatial distribution of the radio wave intensity can be measured.

As described above, according to Embodiment 1, two-dimensional distribution of the intensity of the front surface incident radio wave can be measured in almost real time (in the order of msec) in an extremely short time period (at a high speed). That is to say, the radio wave intensity in a plurality of measurement sections for radio wave can be measured in an extremely short time period.

Furthermore, the size of the cells CL disposed on the front surface of the radio wave absorber 100 is sufficiently smaller than the wavelength of the radio wave emitted from the radio wave source RW10 to the front surface of the radio wave absorber 100, thus higher spatial resolution smaller than the wavelength is obtained. Accordingly, e.g., a fading pattern due to interference between a plurality of radio waves can be measured with a high resolution.

Furthermore, according to the configuration of the radio wave absorber 100 of Embodiment 1, a problem of coupling between antennas, which is encountered when measurement is performed with antennas of an antenna array arranged in close proximity to each other to increase the spatial resolution, does not occur.

Also, according to Embodiment 1, the radio wave absorber 100 is a member which absorbs radio wave, thus the radio wave intensity can be measured without disturbing the spatial distribution of the radio wave (by e.g., reflection) radiated from an object to be measured.

In addition, the radio wave absorber 100 has a size which can be easily carried by a measuring operator, thus can be installed with ease to a measurement location of radio wave, and the spatial distribution of the radio wave of the location can be measured in real time (temporal resolution in the order of msec) conveniently.

Embodiment 2

In Embodiment 2, a radio wave intensity measuring device capable of identifying the polarization direction of a front surface incident radio wave is described.

FIG. 6 is a block diagram showing the configuration of a radio wave intensity measuring device 1002 in Embodiment 2. As shown in FIG. 6, compared with the radio wave intensity measuring device 1000 of FIG. 5, the radio wave intensity measuring device 1002 further includes a data collector 300 and a controller 400. Except for this, the radio wave intensity measuring device 1002 is similar to the radio wave intensity measuring device 1000, thus detailed description is not repeated.

Data collector 300 receives a plurality of measured radio wave intensities from a plurality of measuring circuits 211 included in the measurer 200. The data collector 300 is supposed to have previously recognized the location information of the resistance connected to the measuring circuit 211, the resistance being a transmission source of the radio wave intensity.

Although the details are described later, the data collector 300 transmits the received a plurality of radio wave intensities to the controller 400. The controller 400 is an arithmetic circuit such as a CPU (Central Processing Unit). The controller 400 may be a CPU provided in an external computer.

FIG. 7 is a diagram for illustrating absorption of the electric field of radio wave incident on the front surface of the radio wave absorber 100.

As shown in FIG. 7, on the front surface of the radio wave absorber 100, the resistances (e.g., resistance R11) aligned in the horizontal (X (row)) direction absorb linearly polarized wave in the horizontal direction of the electric field of the front surface incident radio wave. Also, on the front surface of the radio wave absorber 100, the resistances (e.g., resistance R11D) aligned in the vertical (Y (column)) direction absorb linearly polarized wave in the vertical direction of the electric field of the front surface incident radio wave.

In the case where the direction of the electric field of the front surface incident radio wave is a diagonal direction, the electric power of the radio wave is absorbed simultaneously by the resistances aligned in the horizontal and vertical directions.

In Embodiment 2, by using the above-mentioned characteristics, the polarization direction of the front surface incident radio wave (vertical, horizontal, diagonal (upper right diagonal, upper left diagonal, etc.) direction) is identified based on the electric power consumed (absorbed) by the resistances aligned in the horizontal direction, and the electric power consumed (absorbed) by the resistances aligned in the vertical direction.

Specifically, each of the plurality of measuring circuits 211 included in the measurer 200 transmits the power consumption (radio wave intensity) of the corresponding resistance connected with the measuring circuit 211 to the data collector 300. As described above, the data collector 300 is supposed to have previously recognized the location information of the resistance connected to the measuring circuit 211, the resistance being a transmission source of the radio wave intensity. The location information of the resistance is supposed to be the information for identifying the cell CL and the information indicating the connection location of the resistance in the relevant cell CL.

For example, the data collector 300 recognizes that the radio wave intensity received from the measuring circuit 211.1 is the power consumed by the resistance R11 (see FIG. 7) connected to the right side of the cell CL11.

In this case, the location information of the resistance is supposed to be the information for identifying the cell CL (CL11) and the information indicating the connection location (right) of the resistance in the cell CL. The data collector 300 associates the received radio wave intensity with the location information of the resistance at which the radio wave intensity has been measured, then transmits the associated information to the controller 400.

The controller 400 identifies the polarization direction of the front surface incident radio wave by the two radio wave intensities (consumed power) respectively corresponding to two resistances which are connected to the same cell CL and perpendicular to each other.

That is to say, the controller 400 identifies the polarization direction of the front surface incident radio wave based on the radio wave intensity (consumed power) corresponding to the resistance connected to the same cell CL in the horizontal (row) direction, and the radio wave intensity (consumed power) corresponding to another resistance connected to the same cell CL in the vertical (column) direction. That is to say, the controller 400 identifies the polarization direction of the front surface incident radio wave based on the radio wave intensity (consumed power) corresponding to partial resistances aligned in the horizontal (row) direction out of the plurality of resistances disposed on the radio wave absorber 100, and the radio wave intensity (consumed power) corresponding to partial resistances aligned in the vertical (column) direction out of the plurality of resistances disposed on the radio wave absorber 100.

Here, the electric power (consumed power) absorbed by the resistance connected to the cell CL in the horizontal (row) direction is denoted by $P_H$. Also, the electric power (consumed power) absorbed by the resistance connected to the cell CL in the vertical (row) direction is denoted by $P_V$.

For example, the power consumed by the resistance R11 connected to the cell CL11 of FIG. 7 is denoted by the electric power $P_H$. Also, the power consumed by the resistance R11D connected to the CL11 of FIG. 7 is denoted by the electric power $P_V$. In this case, the controller 400 identifies the polarization direction of the front surface incident radio wave based on the electric power $P_H$ and $P_V$.

In the case where the electric power $P_V$ is other than "0" and the electric power $P_H$ is "0", the controller 400 identifies that the front surface incident radio wave is a linearly polarized wave, and the polarization direction of the front surface incident radio wave is the vertical (Y) direction. Also, in the case where the electric power $P_V$ is "0" and the electric power $P_H$ is other than "0", the controller 400 identifies that the front surface incident radio wave is a linearly polarized wave, and the polarization direction of the front surface incident radio wave is the horizontal (X) direction.

Also, in the case where the electric power $P_V$ is other than "0" and the electric power $P_H$ is other than "0", the controller 400 identifies that the front surface incident radio wave is either one of a linearly polarized wave, a circularly polarized wave, or an elliptically polarized wave. In the case where the front surface incident radio wave is a circularly polarized wave or an elliptically polarized wave, electric power is absorbed by the resistances in the horizontal and vertical directions simultaneously, thus the front surface incident radio wave cannot be distinguished from a linearly polarized wave in a diagonal direction. In this case, when the electric power $P_V$ is "0" and the electric power $P_H$ is other than "0" in the state that the radio wave absorber 100 is rotated, for example, 45 degrees in a clockwise direction, the controller 400 identifies that the front surface incident radio wave is a linearly polarized wave, and the polarization direction of the front surface incident radio wave is the direction of rotated vertical axis in the state that the vertical axis is rotated 45 degrees in a counterclockwise direction.

Also, in this case, when the electric power $P_V$ is other than "0" and the electric power $P_H$ is "0" in the state that the radio wave absorber 100 is rotated 45 degrees in a clockwise direction, the controller 400 identifies that the front surface incident radio wave is a linearly polarized wave, and the polarization direction of the front surface incident radio wave is the direction of rotated vertical axis in the state that the vertical axis is rotated 45 degrees in a clockwise direction.

Also, in the case where the values of the electric power $P_V$ and the electric power $P_H$ in the state that the radio wave absorber 100 is rotated a predetermined angle (e.g., 45 degrees in a clockwise direction) maintain the same as before the rotation, the controller 400 determines that the front surface incident radio wave is a circularly polarized wave. However, the rotation direction of the circularly polarized wave cannot be identified.

Also, in the case where the values of the electric power $P_V$ and the electric power $P_H$ in the state that the radio wave absorber 100 is rotated a predetermined angle (e.g., 45 degrees in a clockwise direction) are changed from the values before the rotation, and are other than "0", the controller 400 determines that the front surface incident radio wave is an elliptically polarized wave. However, the rotation direction of the elliptically polarized wave cannot be identified.

In the case where the electric power $P_V$ is other than "0" and the electric power $P_H$ is other than "0", by rotating the radio wave absorber 100 an angle other than 45 degrees, a polarization direction other than the direction of rotated vertical axis in the state that the vertical axis is rotated 45 degrees in a clockwise direction can be identified.

In the case where the electric power $P_V$ is other than "0", and the electric power $P_H$ is "0" in the state that the radio wave absorber 100 is rotated, for example, 30 degrees in a clockwise direction, the controller 400 identifies that the front surface incident radio wave is a linearly polarized wave, and the polarization direction of the front surface incident radio wave is the direction of rotated vertical axis in the state that the vertical axis is rotated 30 degrees in a clockwise direction.

Also, in the case where the electric power $P_V$ is other than "0", and the electric power $P_H$ is "0" in the state that the radio wave absorber 100 is rotated, for example, 60 degrees in a clockwise direction, the controller 400 identifies that the front surface incident radio wave is a linearly polarized wave, and the polarization direction of the front surface incident radio wave is the direction of rotated vertical axis in the state that the vertical axis is rotated 60 degrees in a clockwise direction.

That is to say, the controller 400 is a polarization direction identifying unit that identifies the polarization direction of radio wave.

As described above, according to Embodiment 2, the polarized waves in the vertical and horizontal directions of the electric field of the front surface incident radio wave can be measured simultaneously based on two radio wave intensities (consumed power) corresponding to two resistances which are connected to the same cell CL and perpendicular to each other.

That is to say, the controller 400 can measure the polarized waves in the vertical and horizontal directions of the electric field of the front surface incident radio wave simultaneously based on the radio wave intensity (consumed power) corresponding to the resistance connected to the same cell CL in the horizontal (row) direction, and the radio wave intensity (consumed power) corresponding to another resistance connected to the same cell CL in the vertical (column) direction. That is to say, the controller 400 can measure the polarized waves in the vertical and horizontal directions of the electric field of the front surface incident radio wave simultaneously based on the radio wave intensity (consumed power) corresponding to partial resistances aligned in the horizontal (row) direction out of the plurality of resistances disposed on the radio wave absorber 100, and the radio wave intensity (consumed power) corresponding to partial resistances aligned in the vertical (column) direction out of the plurality of resistances disposed on the radio wave absorber 100.

Therefore, the vertical, horizontal, and diagonal directions of the linearly polarized wave of the front surface incident radio wave can be identified.

The polarization direction of the front surface incident radio wave is not limited to the directions of two resistances which are connected to the same cell CL and perpendicular to each other, and may be identified based on the power consumed by the sum of two or more resistances aligned in the horizontal direction, and the power consumed by the sum of two or more resistances aligned in the vertical direction.

The identification method of the polarization direction of the front surface incident radio wave is not limited to the method described above. When electric power is measured, the phase of the front surface incident radio wave may be measured in addition to the amplitude (radio wave intensity) of the front surface incident radio wave. In this case, the controller 400 can identify whether the front surface incident radio wave is either one of a linearly polarized wave, a circularly polarized wave, or an elliptically polarized wave without rotating the radio wave absorber 100.

In the case where the front surface incident radio wave is a linearly polarized wave, the controller 400 can also identify the polarization direction (for example, the direction of rotated vertical axis in the state that the vertical axis is rotated 45 degrees in a clockwise direction) of the front surface incident radio wave. In the case where the front surface incident radio wave is a circularly polarized wave, the controller 400 can also identify the rotation direction (for example, clockwise direction) of the circularly polarized wave. In the case where the front surface incident radio wave is an elliptically polarized wave, the controller 400 can also identify the rotation direction of the elliptically polarized wave.

Embodiment 3

In Embodiments 1 and 2, the case where the LC parallel circuit resonates and the impedance thereof becomes infinite in the equivalent circuit shown in FIG. 4B occurs only when the frequency of the front surface incident radio wave coincides with the resonance frequency of the LC parallel circuit. For this reason, in Embodiments 1 and 2, the frequency band in which the radio wave absorber 100 can absorb much of the front surface incident radio wave is extremely narrow.

In Embodiment 3, a configuration for expanding the frequency band of the radio wave which can be absorbed by the radio wave absorber, i.e., the radio wave to be measured is described.

In order to expand the frequency band of the radio wave which can be absorbed by the radio wave absorber, the value of L or C may be made variable in the LC parallel circuit. Because L is determined to according to the thickness of the radio wave absorber, C is made variable.

In Embodiment 3, the following radio wave absorber 100A is used instead of the radio wave absorber 100 shown in FIGS. 1, 3, and 5.

Figure 8A:
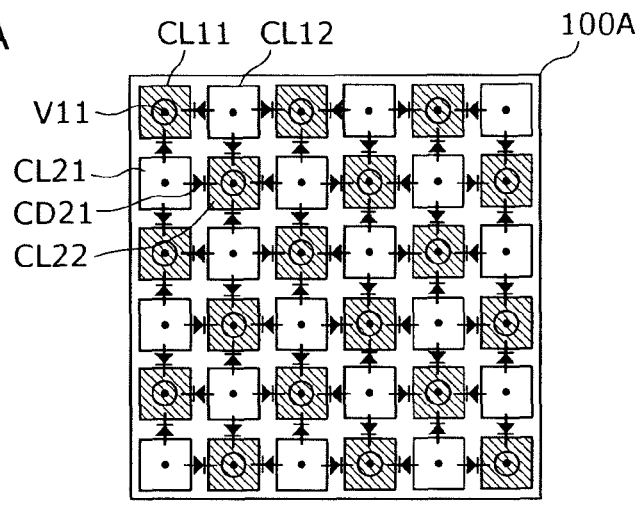
FIG. 8A is a diagram for illustrating a radio wave absorber in Embodiment 3.
Figure 8B:
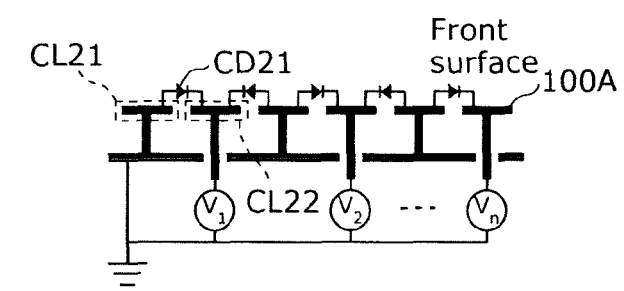
FIG. 8B is a diagram for illustrating the radio wave absorber in Embodiment 3.
Figure 8C:
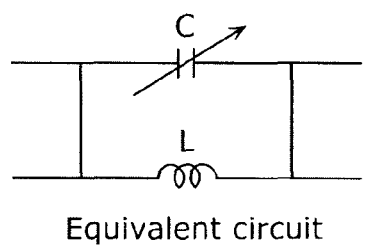
FIG. 8C is a diagram for illustrating the radio wave absorber in Embodiment 3.

FIGS. 8A, 8B, and 8C are diagrams for illustrating the radio wave absorber 100A in Embodiment 3. FIG. 8A is a diagram showing the front surface of the radio wave absorber 100A. Hereinafter, the radio wave entering the front surface of the radio wave absorber 100A is also referred to as the front surface incident radio wave.

As shown in FIG. 8A, compared with the radio wave absorber 100 of FIG. 3, in the radio wave absorber 100A, each pair of adjacent cells CL are electrically connected via a high-frequency variable capacitance diode in addition to a resistance which is not shown. Except for this, the radio wave absorber 100A is similar to the radio wave absorber 100, thus detailed description is not repeated.

FIG. 8B is a diagram simply showing a cross-sectional configuration of the radio wave absorber 100A. In FIG. 8B, the resistances are not shown for the simplicity of the figure. As shown in FIG. 8B, appropriate bias voltage is applied to cell CL alternately for a plurality of cells CL disposed on the front surface of the radio wave absorber 100A. Hereinafter, a cell CL to which bias voltage is applied is referred to as a bias applied cell. Hereinafter, a cell CL connected to the ground is referred to as a ground connected cell.

For example, as shown in FIGS. 8A and 8B, a voltage is applied to the cells CL11 and CL22. That is to say, the cells CL11 and CL22 are bias applied cells. Also, the cells CL12 and CL21 are connected to the ground. That is to say, the cells CL12 and CL21 are ground connected cells. According to this configuration, the capacity of each high-frequency variable capacitance diode (for example, variable capacitance diode CD21) between cells CL can be changed.

When the configuration shown in the radio wave absorber 100A is represented by an equivalent circuit, the LC parallel circuit as shown in FIG. 8C is obtained. That is to say, the radio wave absorber 100A has a plurality of LC parallel circuits capable of changing the resonance frequency.

FIG. 9 is a diagram showing in detail the configuration of the radio wave absorber 100A. As shown in FIG. 9, each pair of adjacent cells CL are electrically connected via the resistances and the capacitors for DC (direct current) cut both connected in series. For example, the cells CL11 and CL12 are electrically connected via a resistance R11 and a capacitor for DC cut C11 both connected in series.

Figure 10:
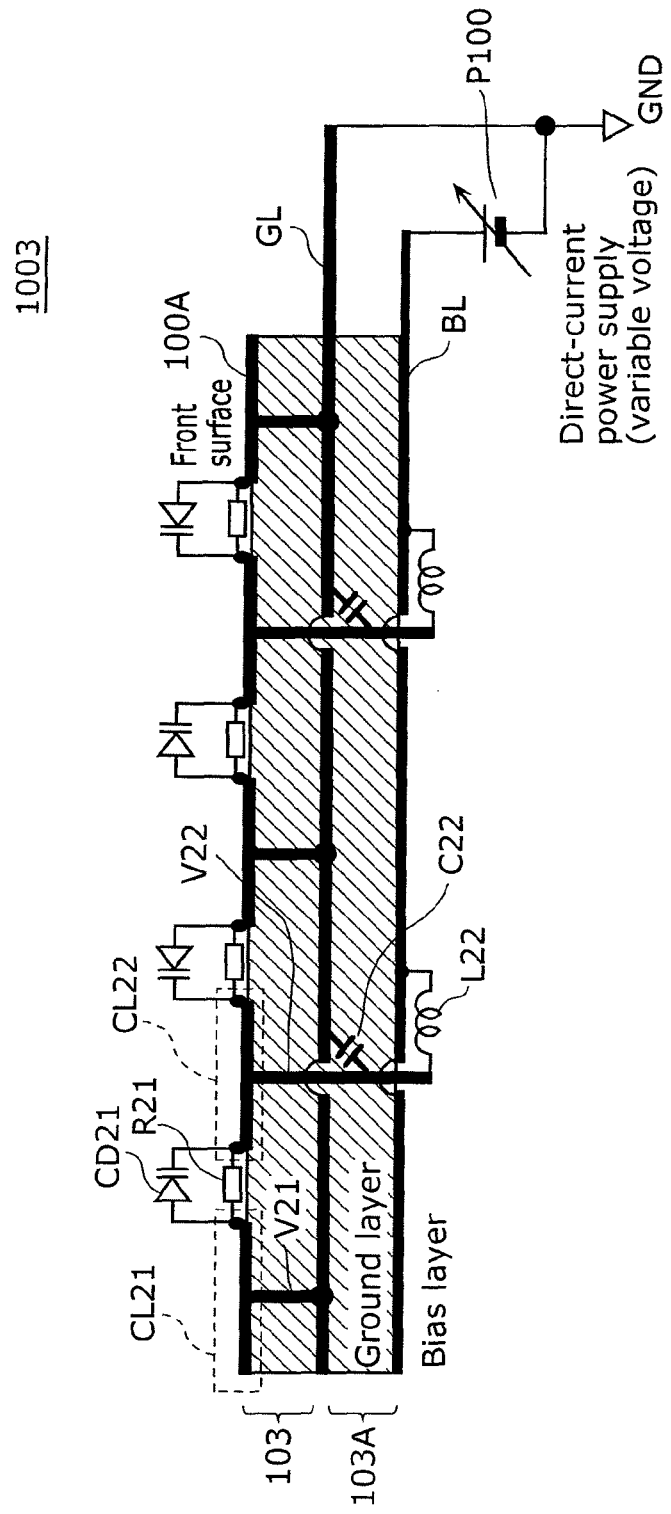
FIG. 10 is a diagram showing in detail the cross-sectional configuration of a radio wave absorber in a radio wave intensity measuring device of Embodiment 3.

FIG. 10 is a diagram showing in detail the cross-sectional configuration of the radio wave absorber 100A in the radio wave intensity measuring device 1003 of Embodiment 3. In FIG. 10, the capacitors for DC cut shown in FIG. 9 are not shown for the simplicity of the figure. Similarly to the radio wave intensity measuring device 1000 of FIG. 5, the radio wave intensity measuring device 1003 includes the measurer 200, but, in FIG. 10, the measurer 200 is not shown for the simplicity of the figure.

As shown in FIG. 10, similarly to the radio wave absorber 100 of FIG. 5, the radio wave absorber 100A has a structure in which a substrate 103A is fixed to the rear surface of a substrate 103 which absorbs radio wave. The radio wave absorber 100A is provided with a ground line GL and a bias line BL.

A direct current power supply P100 is connected to the bias wire BL. The direct current power supply P100 can change the voltage supplied to the bias wire BL. The ground line GL is electrically connected to a ground connected cell (for example, the cell CL21) by a via (for example, a via V21). The bias line BL is electrically connected to a bias applied cell (for example, the cell CL22) by a via (for example, a via V22) through an inductor for noise cut (for example, L22).

Also, a bias applied cell (for example, the cell CL22) is electrically connected to the ground line GL through a via (for example, the via V22) and a capacitor (for example, a capacitor C22).

By the direct current power supply P100 changing the voltage supplied to the bias line BL, the capacity of each high-frequency variable capacitance diode (for example, the variable capacitance diode CD21) between cells CL can be changed.

As described above, according to Embodiment 3, the radio wave absorber 100A has a configuration capable of changing the capacity of each high-frequency variable capacitance diode between cells CL. Accordingly, the resonance frequency of a plurality of LC parallel circuits included in the radio wave absorber 100A can be changed. That is to say, the direct current power supply P100 is a resonance frequency changer that changes the resonance frequency of a resonant circuit.

The radio wave absorber 100A absorbs the front surface incident radio wave at a maximum level (efficiently) when the LC parallel circuit resonates, i.e., the resonance frequency of the LC parallel circuit coincides with the frequency of the front surface incident radio wave.

Therefore, according to Embodiment 3, by making the resonance frequency of the LC parallel circuit variable, the frequency band of the front surface incident radio wave which can be absorbed by the radio wave absorber 100A, i.e., the front surface incident radio wave to be measured can be expanded. That is to say, wide-band radio wave can be measured by controlling the bias voltage. As a result, the radio wave intensity measuring device 1003 can be used for wideband frequency from hundreds of MHz to several GHz.

By sweeping the bias voltage to find the frequency at which the measured value reaches its maximum, the frequency of the front surface incident radio wave can be identified to a certain extent. In this case, the radio wave intensity measuring device 1003 can identify the frequency of a target radio wave like a spectrum analyzer.

Embodiment 4

In Embodiment 4, a radio wave intensity measuring device which has a different configuration from that in Embodiments 1 to 3 is described.

Figure 11:
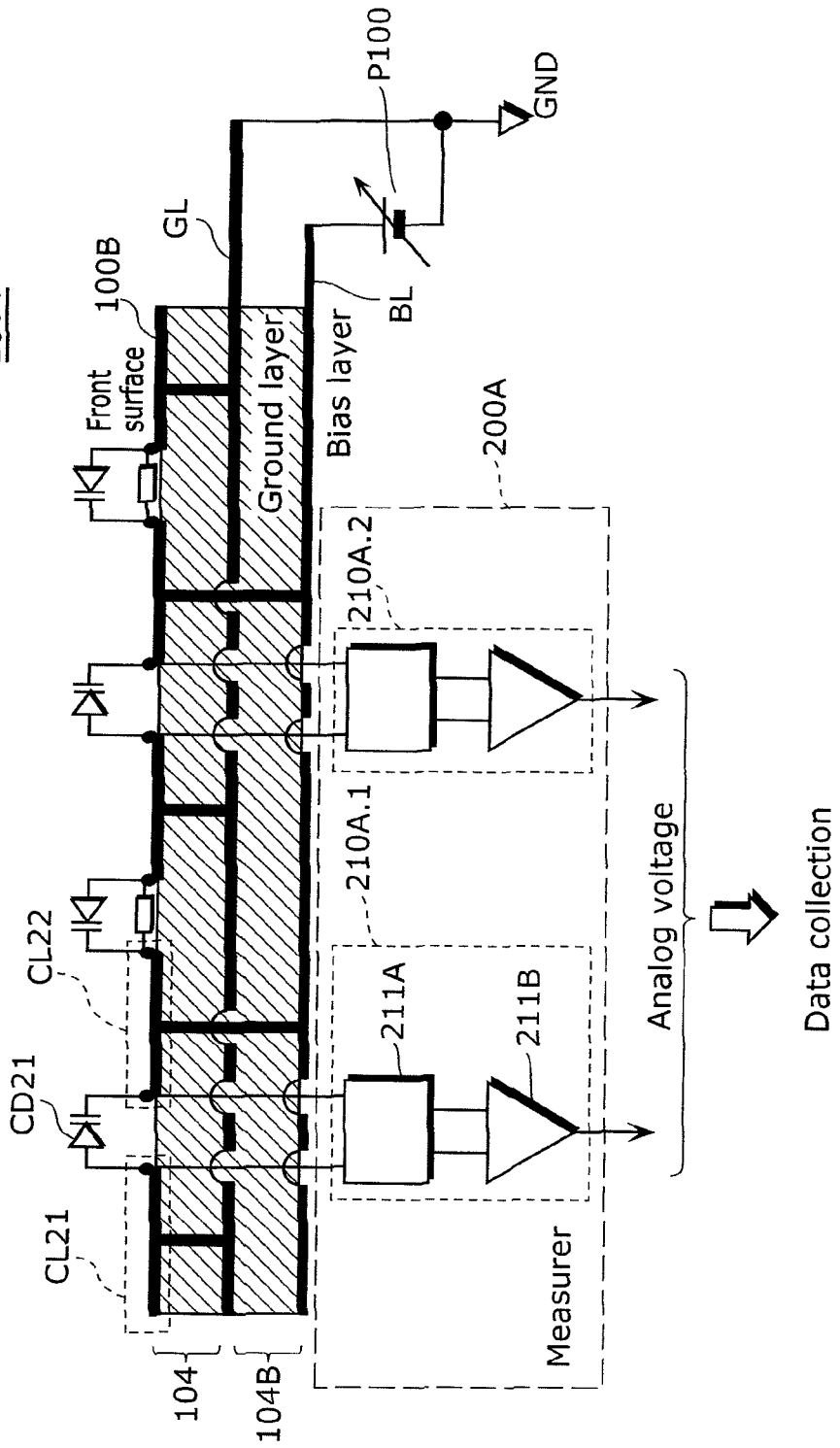
FIG. 11 is a block diagram showing the configuration of a radio wave intensity measuring device in Embodiment 4.

FIG. 11 is a block diagram showing the configuration of a radio wave intensity measuring device 1004 in Embodiment 4. As shown in FIG. 11, compared with the radio wave intensity measuring device 1000 of FIG. 5, the radio wave intensity measuring device 1004 includes a radio wave absorber 100B instead of the radio wave absorber 100, and a measurer 200A instead of the measurer 200. Except for this, the radio wave intensity measuring device 1004 is similar to the radio wave intensity measuring device 1000, thus detailed description is not repeated.

Compared with the radio wave absorber 100A of FIG. 10, in the radio wave absorber 100B, partial resistances out of a plurality of resistances are replaced by measuring circuits 210A (measuring circuits 210A.1, 210A.2, ... ). Except for this, the radio wave absorber 100B is similar to the radio wave absorber 100A, thus detailed description is not repeated. Hereinafter, each of the measuring circuits 210A.1, 210A.2 and ... is also denoted by a measuring circuit 210A.

Hereinafter, the radio wave entering the front surface of the radio wave absorber 100B is also referred to as the front surface incident radio wave. Similarly to the radio wave absorber 100A of FIG. 8A, in the radio wave absorber 100B, bias voltage is applied to cell CL alternately in the vertical and horizontal directions for a plurality of cells CL disposed on the front surface of the radio wave absorber 1008.

For example, the cell CL21 is electrically connected to the ground line GL. That is to say, the cell CL21 is a ground connected cell. Also, the cell CL22 is electrically connected to the bias line BL. That is to say, the cell CL22 is a bias applied cell.

Figure 12:
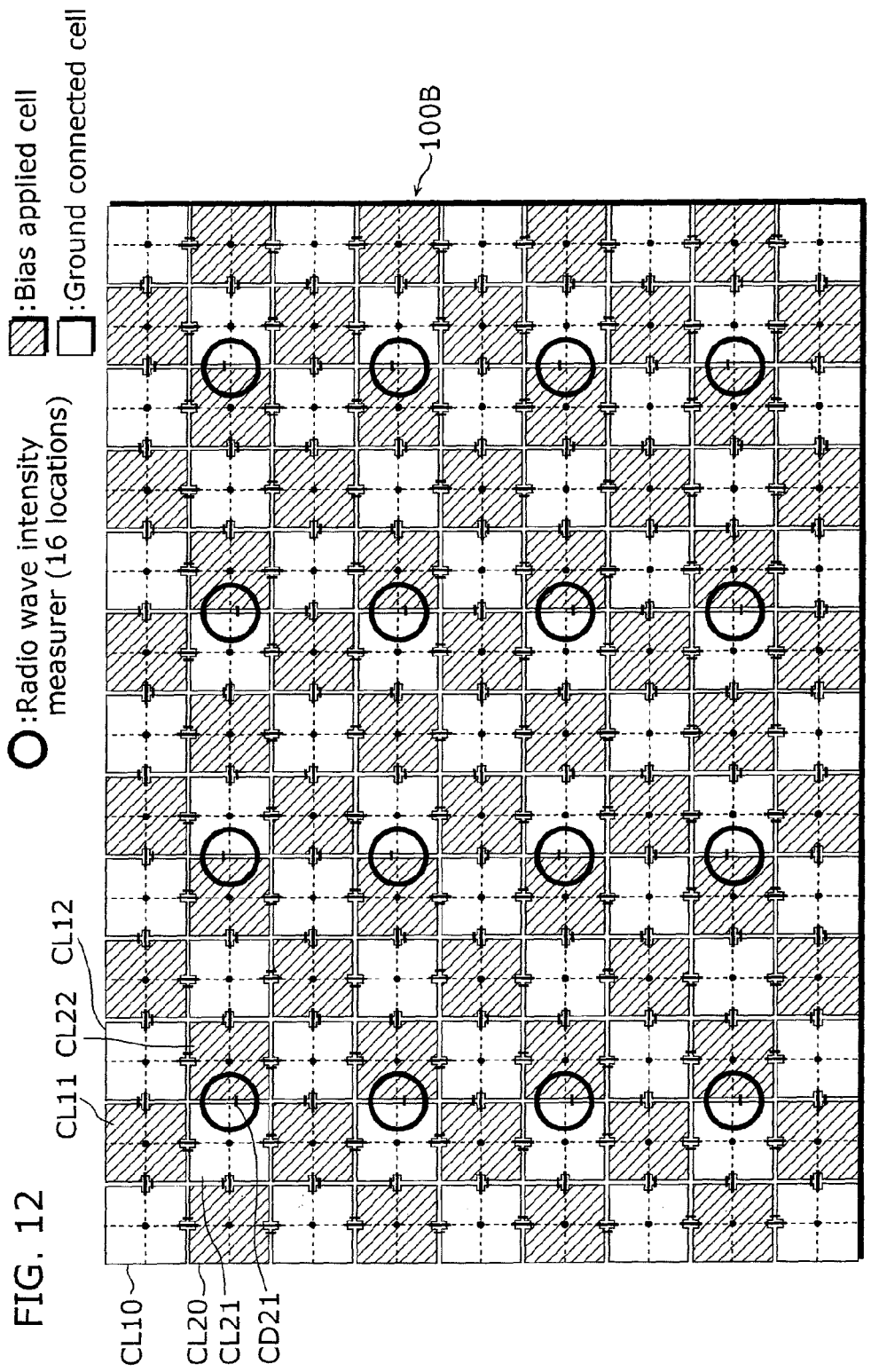
FIG. 12 is a diagram showing the configuration of the front surface of the radio wave absorber.

FIG. 12 is a diagram showing the configuration of the front surface of the radio wave absorber 100B. As shown in FIG. 12, for example, cells CL20, CL11, CL22 are bias applied cells. Also, the cells CL10, CL21, CL12 are ground connected cells.

In 16 circles shown in FIG. 12, only variable capacitance diodes (for example, the variable capacitance diode CD21) are provided.

Also, as shown in FIG. 11, similarly to the radio wave absorber 100A of FIG. 10, the radio wave absorber 100B has a structure in which a substrate 104B is fixed to the rear surface of a substrate 104 which absorbs radio wave.

Figure 13:
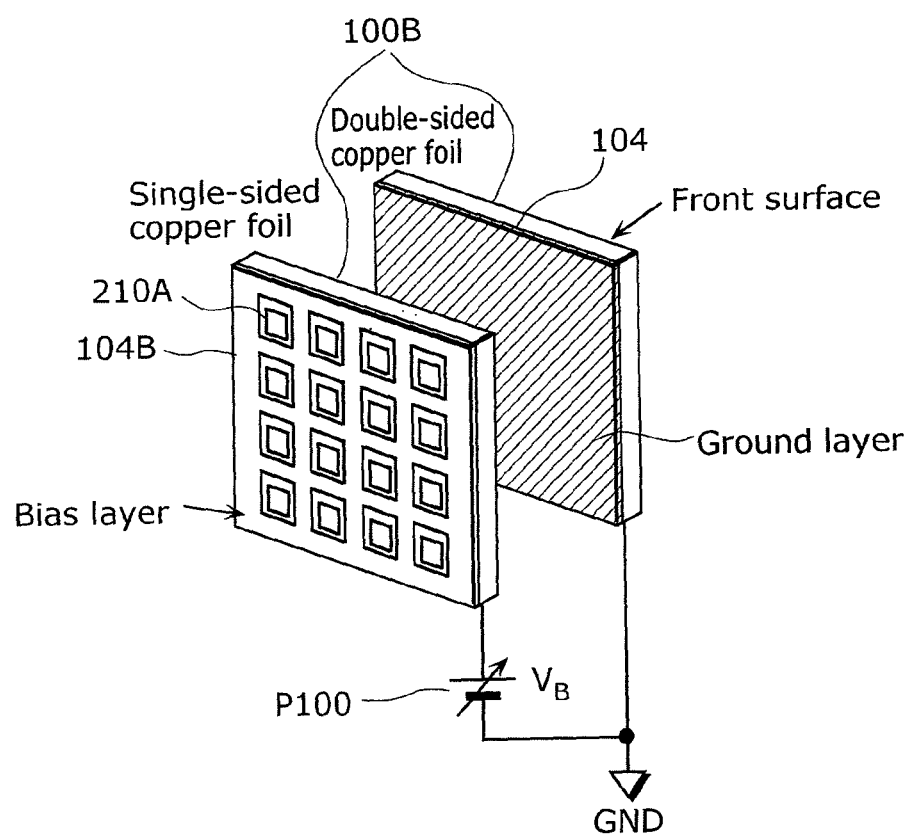
FIG. 13 is a diagram showing the appearance of two substrates included in the wave absorber.

FIG. 13 is a diagram showing the appearance of the substrate 104 and the substrate 104B included in the wave absorber 100B. As shown in FIG. 13, the front surface of the substrate 104 is a surface which absorbs radio wave. A ground layer is formed with copper on the rear surface of the substrate 104. On one side of the substrate 104B, a bias layer is formed, while a measurer 200A including a plurality of measuring circuits 210A is provided.

As shown in FIG. 11, the measurer 200A includes a plurality of measuring circuits 210A (measuring circuits 210A.1, 210A.2, . . . ). As shown in FIG. 11, each measuring circuit 210A is electrically connected to both ends of the variable capacitance diode connected between cells CL. The measuring circuits 210A are connected to only the variable capacitance diodes provided inside the circles shown in FIG. 12. For example, the measuring circuit 210A.1 is electrically connected to both ends of the variable capacitance diode CD21 which connects between the cell CL21 and the cell CL22. That is to say, the measuring circuit 210A.1 is electrically connected to both ends of the cell CL21 and the cell CL22.

Each measuring circuit 210A includes a matching circuit 211A having the same input impedance (for example, 377 ohms) as the impedance of the replaced resistances, and a logarithmic amplifier 211B. For example, the measuring circuit 210A.1 is connected between the cell CL21 and the cell CL22 instead of the resistance R21 of FIG. 10. Each measuring circuit 210A is provided on one surface side of the substrate 104B as shown in FIG. 13.

Also, as shown in FIG. 11, each measuring circuit 210A includes the matching circuit 211A having the same input impedance (for example, 377 ohms) as the impedance of the resistance R21, and the logarithmic amplifier 211B. The matching circuit 211A included in the measuring circuit 210A.1 is connected between the cell CL21 and the cell CL22. The matching circuit 211A is electrically connected to the logarithmic amplifier 211B. The matching circuit 211A consumes the electric power (energy) of the radio wave absorbed in the cell CL connected to the matching circuit 211A.

The logarithmic amplifier 211B logarithmically measures the electric power consumed in the matching circuit 211A, and outputs an analog voltage according to the measured electric power. That is to say, measuring the electric power consumed in the matching circuit 211A with the logarithmic amplifier 211B makes it possible to measure the amount of radio wave absorbed in the corresponding cell CL. That is to say, the intensity of the front surface incident radio wave entering the cell CL corresponding to the matching circuit 211A can be measured by the measuring circuit 210A. Other measuring circuits 210A included in the measurer 200A has a configuration similar to that of the measuring circuit 210A.1, thus detailed description is not repeated.

In the above configuration, by each of a plurality of measuring circuits 210A included in the measurer 200A, the measurer 200A can measure the intensities of the front surface incident radio wave entering the cells CL connected to corresponding variable capacitance diodes simultaneously. Accordingly, on the front surface of the radio wave absorber 100B, the intensities of the front surface incident radio wave at a plurality of locations can be measured simultaneously.

In the case where the amplitude and phase of the front surface incident radio wave is measured, an amplitude and phase measuring circuit is provided in the radio wave intensity measuring device 1004. In this case, after the amplitude and phase measuring circuit is provided in the radio wave intensity measuring device 1004, a frequency conversion circuit may be further provided therein.

Embodiment 5

In Embodiment 5, a radio wave intensity measuring system capable of applying a voltage to a radio wave absorber and collecting data of the intensity of the front surface incident radio wave is described.

Figure 14:
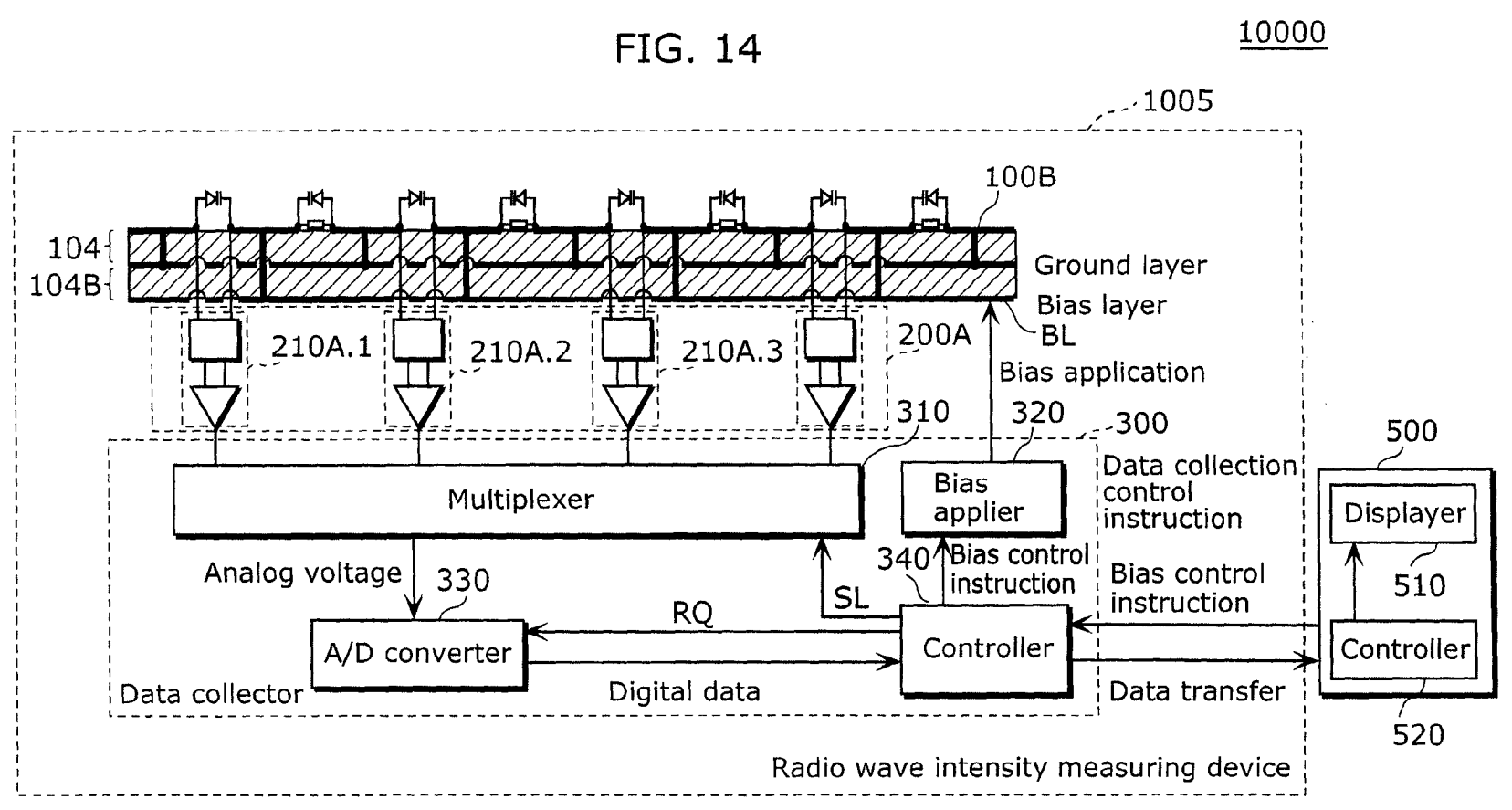

FIG. 14 is a block diagram showing the configuration of a radio wave intensity measuring system 10000 in Embodiment 5.

As shown in FIG. 14, the radio wave intensity measuring system 10000 includes a radio wave intensity measuring device 1005 and a display device 500.

The radio wave intensity measuring device 1005 further includes a data collector 300 as compared with the radio wave intensity measuring device 1004 of FIG. 11. Except for this, the radio wave intensity measuring device 1005 is similar to the radio wave intensity measuring device 1004, thus detailed description is not repeated.

The data collector 300 scans and collects a plurality of radio wave intensities measured by a respective plurality of measuring circuits 210A included in the measurer 200A, and outputs the data of the collected radio wave intensities. The data collector 300 includes a multiplexer 310, a bias applier 320, an A/D converter 330, and a controller 340.

The multiplexer 310 outputs indicated signal out of a plurality of input signals. The multiplexer 310 is connected to a plurality of measuring circuits 210A included in the measurer 200A. The multiplexer 310 transmits a signal to A/D converter 330, the signal having an analog voltage measured by the measuring circuit 210A designated by a selection instruction from the outside out of a plurality of measuring circuits 210A connected.

The A/D converter 330 converts the voltage level of the signal received from the multiplexer 310 to digital data, and transmits the converted digital data (hereinafter referred to as radio wave intensity data) to the controller 340. The controller 340 is an arithmetic circuit such as a CPU (Central Processing Unit). The controller 340 controls each component in the data collector 300.

Communication between the data collector 300 and the display device 500 is performed using a communication cable. Communication between the data collector 300 and the display device 500 may be performed wirelessly (for example, by a wireless LAN (Local Area Network)).

The bias applier 320 is e.g., a D/A converter. The bias applier 320 applies a bias to the bias line BL of the radio wave absorber 100B according to an instruction from the controller 340.

The display device 500 is a PC (Personal Computer) as an example. The display device 500 includes a displayer 510 and a controller 520. The displayer 510 is a device for displaying an image. The controller 520 is an arithmetic circuit such as a CPU (Central Processing Unit). The controller 520 controls each component in the display device 500. The controller 520 performs processing for controlling each component of the data collector 300.

Next, processing by the control of the controller 520 for collecting the data of the intensity of the front surface incident radio wave is described.

First, the controller 520 transmits a bias control instruction to the controller 340. The bias control instruction is an instruction for the bias applier 320 in the data collector 300 to apply designated bias (for example, 3V) to the bias line BL of the radio wave absorber 100B. That is to say, the bias control instruction is an instruction for setting the resonance frequency in each cell CL disposed on the front surface of the radio wave absorber 100B to a specific frequency. The controller 340, when receiving a bias control instruction, transmits the received bias control instruction to the bias applier 320.

In response to the reception of the bias control instruction, the bias applier 320 applies a bias (for example, 3V) designated by the bias control instruction to the bias line BL of the radio wave absorber 100B. Thereby, the designated bias (for example, 3V) is applied to partial cells CL (for example, cells CL11, CL22) out of a plurality of cells CL on the front surface of the radio wave absorber 100B. The designated bias may be applied to all cells CL on the front surface of the radio wave absorber 100B.

Thereby, the resonance frequency in each cell CL disposed on the front surface of radio wave absorber 100B is set to a specific frequency. That is to say, the frequency of the front surface incident radio wave absorbed on the front surface of the radio wave absorber 100B is controlled. That is to say, the controller 520 controls the frequency of the front surface incident radio wave absorbed on the front surface of the radio wave absorber 100B by a bias control instruction.

Also, the controller 520 transmits a data collection control instruction to the controller 340. The data collection control instruction is an instruction for collecting the data of intensity of the front surface incident radio wave from the data collector 300.

In response to reception of a data collection control instruction, the controller 340 transmits a data request instruction RQ to the A/D converter 330. The data request instruction RQ is an instruction for requesting data to the A/D converter 330.

In response to reception of the data collection control instruction, the controller 340 also performs selection instruction transmission processing. In the selection instruction transmission processing, a selection instruction SL is transmitted to the multiplexer 310. The selection instruction SL is an instruction for designating a measuring circuit 210A to be connected to the multiplexer 310.

In response to reception of the selection instruction SL, the multiplexer 310 transmits a signal to the A/D converter 330, the signal having an analog voltage measured by the measuring circuit 210A designated by the selection instruction SL. The voltage of the signal received by the A/D converter 330 shows the intensity of the radio wave entering the cell CL corresponding to the measuring circuit 210A.

The A/D converter 330 converts the voltage level of the received signal to radio wave intensity data as digital data, and transmits the converted radio wave intensity data to the controller 340. Thereby, the controller 340 receives the radio wave intensity data of the voltage measured by the measuring circuit 210A designated by the selection instruction SL. The radio wave intensity data shows the intensity of radio wave entering the cell CL corresponding to the measuring circuit 210A designated by the selection instruction SL.

The controller 340 repeats the above-mentioned selection instruction transmission processing until the controller 340 receives all the radio wave intensity data of the voltages measured by the measuring circuits 210A connected to the variable capacitance diodes in all the circles shown in FIG. 12. In this case, each time as the selection instruction transmission processing is repeated, the controller 340 transmits a selection instruction SL for designating a different measuring circuit 210A.

Each time as the selection instruction transmission processing is repeated, the controller 340 transmits a selection instruction SL, for example, designating the measuring circuit 210A connected to the variable capacitance diode in the circle one place on the right (1st row, 2nd column) from the upper left (1st row, 1st column) circle, out of the plurality of circles shown in FIG. 12. In the case where no circle exists on the right, in the selection instruction transmission processing, a selection instruction SL is transmitted for designating the measuring circuit 210A connected to the variable capacitance diode in the leftmost circle on the next row.

Finally, a selection instruction SL is transmitted for designating the measuring circuit 210A connected to the variable capacitance diode in the lower right circle (4th row, 4th column) in the plurality of circles shown in FIG. 12. By this processing, the controller 340 acquires 16 radio wave intensity data of the voltages measured by the measuring circuits 210A connected to the variable capacitance diodes in all the circles shown in FIG. 12.

Each selection instruction transmission processing is terminated in an extremely short time. Accordingly, the controller 340 acquires 16 radio wave intensity data in an extremely short time, i.e., almost simultaneously. Hereinafter, data including all the radio wave intensity data received by repeating the selection instruction transmission processing is referred to as radio wave intensity distribution data.

The controller 340 then transmits the radio wave intensity distribution data to the controller 520.

By the above processing, the display device 500 can acquire in an extremely short time, i.e., almost simultaneously radio wave intensity distribution data showing the radio wave intensity of the front surface incident radio wave entering the cells CL at a plurality of locations (the plurality of cells CL corresponding to the respective plurality of measuring circuits 210A included in the measurer 200A) on the front surface of the radio wave absorber 100B.

As described above, according to Embodiment 5, the radio wave intensity distribution data showing the radio wave intensity of the front surface incident radio wave entering the cells CL at a plurality of locations on the front surface of the radio wave absorber 100B, can be acquired in an extremely short time, i.e., almost simultaneously.

In Embodiment 5, the processing for serially acquiring radio wave intensity data of a plurality of voltages measured by a plurality of measuring circuits 210A included in the measurer 200A has been described, but, a configuration may be made such that the radio wave intensity data of a plurality of voltages measured by the respective plurality of measuring circuits 210A is acquired simultaneously.

A configuration may be made such that an A/D conversion function is provided to a plurality of measuring circuits 210A included in the measurer 200A, and the measurer 200A sends digital data to the controller 340 via wired or wireless communications. In this case, the A/D converter 330 included in the data collector 300 is not needed.

Embodiment 6

In Embodiment 6, processing for generating an image showing the intensity distribution of radio wave and displaying the generated image is described.

The radio wave intensity measuring system in Embodiment 6 is similar to the radio wave intensity measuring system 10000 in FIG. 14, thus detailed description is not repeated.

The controller 520 of the display device 500, when acquiring radio wave intensity distribution data by the processing described in Embodiment 5, generates a radio wave intensity distribution image based on the radio wave intensity distribution data. That is to say, the controller 520 is an image generator that generates an image.

The radio wave intensity distribution image shows a two-dimensional distribution of intensities of the front surface incident radio wave to the cells CL at a plurality of locations on the front surface of the radio wave absorber 100B, the intensities being measured by the respective plurality of measuring circuits 210A included in the measurer 200A. That is to say, the radio wave intensity distribution image is a visualized image of the intensities of the front surface incident radio wave measured at the associated locations of the plurality of measurement sections (cells CL).

Here, the radio wave intensity distribution image generated by the controller 520 is assumed to be the following radio wave intensity distribution image G110. In this case, the controller 520 displays the generated radio wave intensity distribution image G110 on the displayer 510.

Figure 15:
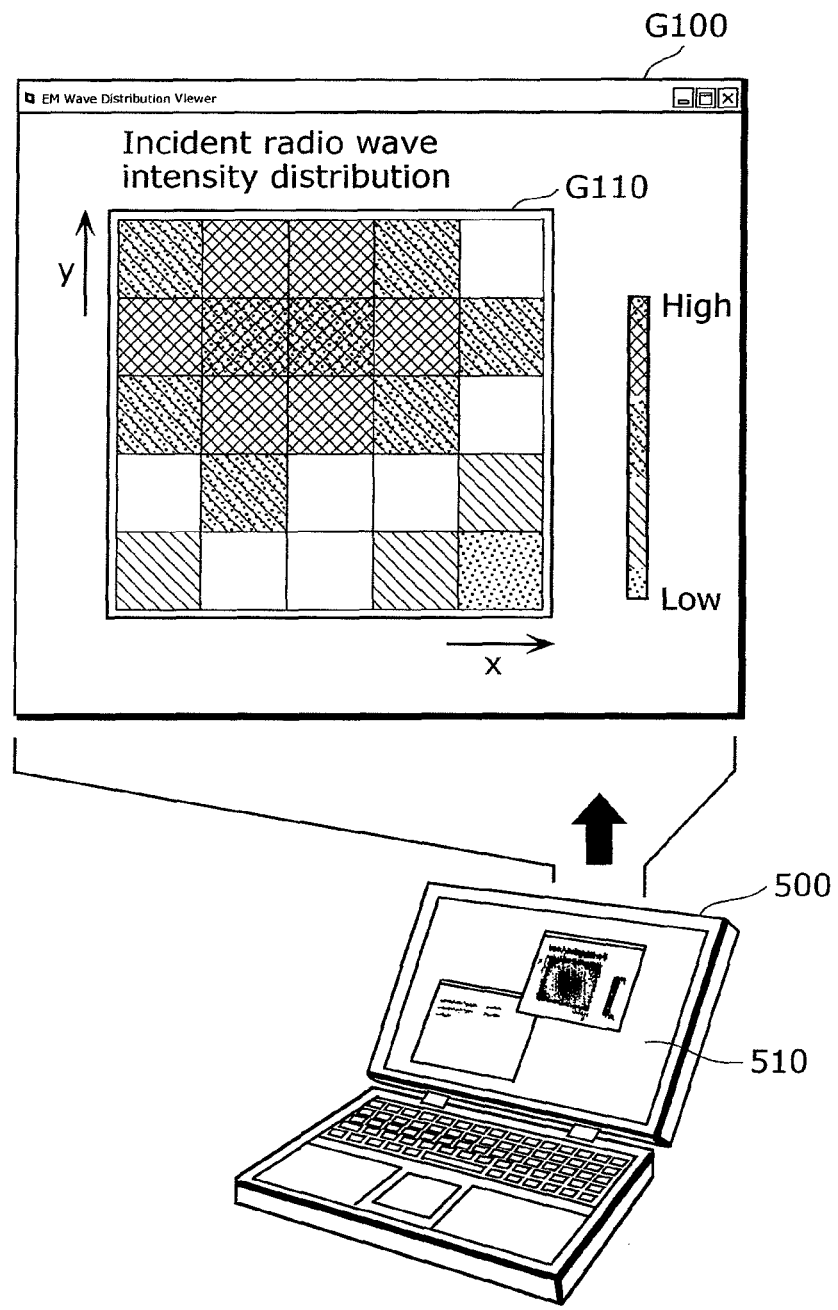
FIG. 15 is a diagram showing the state in which a radio wave intensity distribution image is displayed on a displayer of the display device.

FIG. 15 is a diagram showing a state in which the radio wave intensity distribution image G110 is displayed on the displayer 510 of the display device 500. As shown in FIG. 15, a window image G100 in which the radio wave intensity distribution image G110 is placed is displayed on the displayer 510.

The radio wave intensity distribution image G110 is not for the case of 16 measurement locations as shown in FIG. 12, but for the case of 25 measurement locations as an example. The radio wave intensity distribution image G110 represents the intensity of the front surface incident radio wave at measurement location (cell CL) with colors.

Here, the radio wave intensity is represented, for example, in terms of ten levels from 1 to 10. The radio wave intensity "10" is assumed to be the greatest radio wave intensity. In this case, in the radio wave intensity distribution image G110, the measurement locations (cells CL) whose radio wave intensities are "10", "8", "6", "4", "1" are shown by red, orange, yellow, blue, purple, respectively.

As described above, by displaying the radio wave intensity distribution image G110 on the displayer 510, the two-dimensional distribution of the intensities of the front surface incident radio wave to the cells CL at a plurality of locations on the front surface of the radio wave absorber 100B can be visualized.

Next, the processing for displaying time-varying radio wave intensity distribution image as an animation is described.

In this case, the controller 520 of the display device 500 performs processing for acquiring the radio wave intensity distribution data described in Embodiment 5 for every predetermined time period (for example, $1/15$ second). Because the processing for acquiring the radio wave intensity distribution data has been described in Embodiment 5, description is not repeated.

In this case, the controller 520 acquires radio wave intensity distribution data for every predetermined time period (for example, $1/15$ second). The controller 520, each time acquiring radio wave intensity distribution data, generates a radio wave intensity distribution image based on the acquired radio wave intensity distribution data, and displays the generated radio wave intensity distribution image on the displayer 510. That is to say, different radio wave intensity distribution image is displayed on the displayer 510 for every predetermined time period (for example, $1/15$ second). That is to say, the displayer 510 displays the radio wave intensity distribution image generated by the controller 520 for every predetermined time period, while updating the radio wave intensity distribution image.

Therefore, the state of temporal change of two-dimensional distribution of the intensities of the front surface incident radio wave to the cells CL at a plurality of locations on the front surface of the radio wave absorber 100B can be visualized in real time.

The radio wave intensity distribution image generated by the controller 520 may be with each polarization direction of the front surface incident radio wave identified by the method described in Embodiment 2, the polarization direction being represented by an arrow.

In Embodiment 5, an example has been described, in which radio wave intensity distribution data is acquired for every predetermined time period, and a radio wave intensity distribution image based on the radio wave intensity distribution data is displayed for every predetermined time period. However, without being limited to the above embodiment, the radio wave intensity distribution data may be acquired sequentially at a higher rate than the predetermined time period, and the acquired a plurality of pieces of radio wave intensity distribution data may be once stored in e.g., a memory.

In this case, a radio wave intensity distribution image based on each radio wave intensity distribution data may be sequentially displayed on the displayer 510 based on the plurality of pieces of radio wave intensity distribution data stored in the memory. By setting the measurement interval for radio wave intensity distribution image to e.g., 1 millisecond, and setting the display interval to e.g., $1/15$ second, the radio wave intensity distribution images may be replayed in slow-motion.

In the above, the radio wave intensity measuring device and the radio wave intensity measuring system according to the present invention have been described using Embodiments 1 to 6, but, the present invention is not limited to these embodiments. An embodiment made by applying various modifications which may occur to those skilled in the art for each Embodiment, and an embodiment constructed and achieved by combining some components freely in each Embodiment are also included in the present invention.

For example, the measurer (for example, the measurer 200) that measures the intensity of the front surface incident radio wave may be provided with a function of displaying the measured intensity. In this case, the intensity of the front surface incident radio wave may be displayed using brightness variation of an LED or color variation of a full color LED. Alternatively, displayed color may be changed depending on different polarized wave of the front surface incident radio wave.

In this manner, two-dimensional distribution of the intensities of the front surface incident radio wave at a plurality of locations can be visualized by using e.g., an LED, but without using a PC. In this case, the cost of the radio wave intensity measuring system can be reduced.

As described above, the state of the two-dimensional distribution represented by use of e.g., an LED of the intensity of the front surface incident radio wave at a plurality of locations may be captured by a video camera, and may be recorded and stored.

INDUSTRIAL APPLICABILITY

The present invention is suitable for the case where a spatial distribution of radiated radio wave noise is measured in real time for EMC (Electro-Magnetic Compatibility) (electromagnetic environment) measurement in development stage of an electronic device. Also, the present invention is suitable for the case where a radiation pattern is conveniently measured in the development of an antenna.

In addition, the present invention is suitable for the case where a spatial distribution of radio wave intensity is measured in real time in a real room environment in which a wireless transmitter such as a cellular phone, wireless LAN is used. In other words, the present invention is expected to provide a great impact on the field of EMC, antenna, and propagation.

REFERENCE SIGNS LIST

CL11, CL12, CL21, CL22 Cell
R11 Resistance
CD21 Variable capacitance diode
P100 Direct current power supply
G110 Radio wave intensity distribution images
100, 100B Radio wave absorber
200, 200A Measurer
211, 210A Measuring circuit
300 Data Collector
340, 400, 520 Controller
500 Display device
510 Displayer
1000, 1002, 1003, 1004, 1005 Radio wave intensity measuring device
10000 Radio wave intensity measuring system

The invention claimed is:

1. A radio wave intensity measuring device for measuring a radio wave intensity, said radio wave intensity measuring device comprising:
a radio wave absorber that has a plane with a plurality of measurement sections, and is configured to absorb the radio wave incident on the plane; and
a measurer configured to measure radio wave intensities in the plurality of measurement sections,
wherein a measuring member is disposed in a neighborhood of each of the measurement sections,
said measurer is configured to measure the radio wave intensities in the respective measurement sections by using the measuring member disposed in the neighborhood of each of the measurement sections,
the plurality of measuring members are disposed in a matrix form, and
said radio wave intensity measuring device further comprises a polarization direction identifying unit configured to identify a polarization direction of radio wave based on an intensity of the radio wave measured by said measurer which uses partial measuring members aligned in a row direction out of the plurality of measuring members, and an intensity of the radio wave measured by said measurer which uses partial measuring members aligned in a column direction out of the plurality of measuring members.

2. The radio wave intensity measuring device according to claim 1,
wherein said wave absorber includes a plurality of resonant circuits that absorb radio wave at a maximum level when a resonance occurs; and
further includes a resonance frequency changer that changes a resonance frequency of each of the resonant circuits.

3. The radio wave intensity measuring device according to claim 1,
wherein said measurer includes a plurality of measuring circuits that measure respective radio wave intensities in the plurality of measurement sections almost simultaneously.

4. The radio wave intensity measuring device according to claim 3, further comprising
a data collector configured to scan and collect a plurality of radio wave intensities measured by the respective measuring circuits.

5. A radio wave intensity measuring system including the radio wave intensity measuring device according to claim 4, and a display device,
wherein the radio wave intensity measuring device further comprises
a transmitter configured to transmit the plurality of radio wave intensities collected by said data collector to said display device;
said display device includes
an image generator configured to generate a radio wave intensity distribution image which is an image visualized by associating the plurality of radio wave intensities with respective locations of the measurement sections based on the plurality of radio wave intensities received from said transmitter; and
a displayer configured to display the radio wave intensity distribution image generated by said image generator.

6. The radio wave intensity measuring system according to claim 5,
wherein the plurality of measuring circuits measure respective radio wave intensities in the plurality of measurement sections for every predetermined time period,
said image generator is configured to generate the radio wave intensity distribution image based on the plurality of radio wave intensities measured by the respective plurality of measuring circuits for every predetermined time period, and
said displayer is configured to display the radio wave intensity distribution image generated by said image generator for every predetermined time period, while updating the radio wave intensity distribution image.

* * * * *